United States Patent
Li et al.

(10) Patent No.: US 9,006,666 B2
(45) Date of Patent: Apr. 14, 2015

(54) POSITRON TOMOGRAPHY IMAGING APPARATUS AND METHOD FOR MULTIPHASE FLOW

(75) Inventors: Hongdi Li, Pearland, TX (US); Jige Chen, Gansu (CN)

(73) Assignees: Lanzhou Haimo Technologies Co., Ltd., Lanzhou, Gansu (CN); Hongdi Li, Pearland, TX (US)

(*) Notice: Subject to any disclaimer, the term of this patent is extended or adjusted under 35 U.S.C. 154(b) by 162 days.

(21) Appl. No.: 13/976,385

(22) PCT Filed: Jan. 20, 2011

(86) PCT No.: PCT/CN2011/000094
§ 371 (c)(1),
(2), (4) Date: Aug. 13, 2013

(87) PCT Pub. No.: WO2012/027945
PCT Pub. Date: Mar. 8, 2012

(65) Prior Publication Data
US 2013/0313437 A1 Nov. 28, 2013

(30) Foreign Application Priority Data

Dec. 29, 2010 (CN) .......................... 2010 1 0612053
Dec. 29, 2010 (CN) ...................... 2010 2 0687413 U (51) Int. Cl.
G01T 1/16 (2006.01)
G01N 23/04 (2006.01)
G01T 1/20 (2006.01)
G01T 1/24 (2006.01)

(52) U.S. Cl.
CPC .................. G01T 1/16 (2013.01); G01N 23/046 (2013.01); G01T 1/20 (2013.01); G01T 1/249 (2013.01);
(Continued)

(58) Field of Classification Search
CPC ................. G01N 2223/1013; G01N 2223/628; G01N 23/046; G01N 2223/419; G01T 1/16; G01T 1/249
USPC ..................................................... 250/363.03
See application file for complete search history.

(56) References Cited

U.S. PATENT DOCUMENTS 5,880,375 A * 3/1999 Bielski et al. .............. 73/861.05
6,184,530 B1 2/2001 Hines et al.
(Continued)

FOREIGN PATENT DOCUMENTS

CN 1182873 A 5/1998
CN 1920595 A 2/2007
(Continued)

OTHER PUBLICATIONS

Office Action in corresponding Chinese Application No. 201010612053.0, dated Aug. 4, 2014.
(Continued)

*Primary Examiner* — Marcus Taningco
(74) *Attorney, Agent, or Firm* — Knobbe, Martens, Olson & Bear, LLP (57) ABSTRACT

The present invention relates to a positron tomography imaging apparatus for a multiphase flow in an oil pipeline, which apparatus utilizes positron and electron annihilation generating a pair of coincidence gamma-rays of 511 keV energy as tomography imaging means and provides an on-line tomography imaging function for metering a multiphase flow in an oil pipeline of an oil field. The apparatus comprises a plurality of sets of parallel high-precision gamma-ray detector arrays with a particular space structure arrangement, a positron radioactive source and a shield, and can acquire a phase fraction of such multiphase flow mixture as oil, gas and water under a condition of a single radioactive source by combining an image processing function. The design of a plurality of sets of high-precision detector arrays also greatly improves accuracy of a multiphase flow metering and its applicability in multiphase flows of different flow patterns. The video information of fluid generated by it will significantly enrich oil, gas metering information for petroleum industry and provide basic data for a more effective reservoir management and production optimization.

11 Claims, 5 Drawing Sheets

(52) U.S. Cl.
CPC .. *G01N 2223/1013* (2013.01); *G01N 2223/501* (2013.01); *G01N 2223/628* (2013.01); *G01N 2223/64* (2013.01); *G01N 2223/419* (2013.01)

(56) References Cited

U.S. PATENT DOCUMENTS

| | | | |
|---|---|---|---|
| 7,105,805 B2 * | 9/2006 | Berard et al. | 250/256 |
| 7,649,977 B2 | 1/2010 | Johnson | |
| 7,732,773 B2 | 6/2010 | Mihailescu et al. | |

FOREIGN PATENT DOCUMENTS

| | | |
|---|---|---|
| CN | 101261236 A | 9/2008 |
| CN | 101334454 A | 12/2008 |
| CN | 202092697 U | 12/2011 |
| WO | WO 2006/037169 A2 | 4/2006 |

OTHER PUBLICATIONS

Orito, R. et al. 2003 "A novel design of the MeV gamma-ray imaging detector with Micro-TPC" *Nuclear Instruments and Methods in Physics Research Section A: Accelerators, Spectrometers, Detectors and Associated Equipment* vol. 513, Issues 1-2, pp. 408-412.

Ma, Min 2007 "Investigating Multi-Phase Pipe Flow Measurement Technology Based on γ-Ray" Ph.D. Dissertation, published in China Academic Journal (CD) Electronic Journals Publishing House Co. Ltd. (in 119 pages).

* cited by examiner

POSITRON TOMOGRAPHY IMAGING APPARATUS AND METHOD FOR MULTIPHASE FLOW

TECHNICAL FIELD

The present invention relates to a positron tomography imaging apparatus for multiphase flow in an oil pipeline, i.e. a positron tomography imaging apparatus for a multiphase flow which utilizes a pair of coincidence gamma rays generated by the annihilation of positron and electron to reconstruct an on-line tomography image for the multiphase fluid in the pipeline, and further relates to a method for deriving the multiphase fraction data with positron tomography imaging of a multiphase flow in an oil pipeline.

BACKGROUND ART

The multiphase flow meter has gradually replaced the conventional testing separator owing to such advantages as low investment, low operational cost and unnecessary for separating oil well products. The multiphase flow meter may provide on-line and real-time flow rates and phase fractions of oil, gas and water and provide basic metering data for an oil company to understand actual production condition and capacity of each single well and perform effective reservoir management and production optimization management.

Among many multiphase flow metering technologies, the phase fraction measurement technology based on gamma-rays has become a dominant technology in multiphase metering. At present, the gamma measurement technology used in multiphase metering utilizes single energy or dual gamma-ray energies to acquire an average absorption coefficient of fluid with respect to gamma-rays. As the respective absorption coefficient of oil, gas and water with respect to gamma-rays of a certain energy is definite, in a two-phase flow, single gamma-ray energy is used to acquire an average absorption coefficient to obtain percentages of two components in a mixture (gas and liquid content or water and oil content); dual gamma-ray energies are used to acquire two average absorption coefficients to obtain percentages of three components in a mixture, i.e. phase fraction of a three-phase mixed fluid (gas content, oil content and water content).

At present, the multiphase metering technology based on gamma-rays is mainly confronted with the following limitations and challenges: (1) the measurement accuracy is not high enough. As gamma-ray measurement technology needs to satisfy such a premise as a narrow-beam condition, it is only possible to acquire the components of a mixture within a very small solid angle between a radioactive source and a probe, but nothing can be done about the portions beyond such detection interval. Such method by replacing a whole by a part allows the measurement result to have requirements for overall homogeneity of fluid, which thereby also relatively reduces the whole measurement accuracy. (2) The spatial symmetry is poor. As the gamma-ray narrow-beam in a multiphase flow meter is of a conical structure, the space density of the rays is very high when proximate to a radioactive source (a cone roof), i.e. the fluid is frequently detected, while the density of the rays becomes thinner when proximate to a receiving end (a cone bottom) of the gamma-ray. Thereby, even for a mixture of oil, gas and water of the same average density within a cone, if it has different space distributions in a cone, its measured average densities may also be different. (3) The required measurement time is very long. In order to reduce measurement errors brought by the aforementioned problems (1) and (2), the multiphase flow metering needs averaging many times of instantaneous measurement results so that the measurement time required for one data point is quite long. Such averaging depending on ergodic statistic solves the problem of asymmetry in measurement space, but its effect in reducing the whole non-homogeneity affect is not ideal. (4) Under an extreme flow condition, the metering accuracy of certain single-phase flow may be greatly reduced. At present, the multiphase metering technology bases on measurement of the total flow and the phase fraction and then obtain a flow rate of each single-phase through calculation; when certain single-phase is relatively less (the single-phase phase fraction is relatively lower), the metering accuracy of said phase is relatively poor. (5) It is impossible to obtain flowing behavior of a fluid flow pattern. The present gamma multiphase flow metering all can only provide average density information of a multiphase flow rather than position information of its specific space distribution. Thereby, it is impossible to provide space distribution information, i.e. imaging information, of oil, gas and water inside an oil pipeline.

One object of the present invention is to image a tomography of oil, gas and water inside an oil pipeline so as to obtain dynamic properties of a fluid flow pattern to form a real time video. This video information of fluid may provide richer metering information for petroleum industry such as to more effectively perform reservoir management and production optimization management. The position information of each single-phase fluid in a tomography image may also reduce the dependency on space distribution of flow patterns in the aforementioned absorption calculation as well as metering accuracy under an extreme flow condition, and thus may also greatly improve the measurement accuracy of phase fraction, which is also another object of the present invention. As the invention may improve the measurement accuracy, with respect to the original measurement accuracy, it is equivalent that the measurement time of each testing time is reduced.

The present imaging research on a multiphase flow uses technologies measuring medium features such as electrics/ERT, optics, ultrasound and magnetic resonance, such technologies all have their respective disadvantages and have not gained a successful application in the field of multiphase metering. The present invention uses gamma-ray imaging technology in nuclear medicine combined with relevant image processing technologies so as to effectuate tomography of a multiphase flow in an oil pipeline.

SUMMARY OF THE INVENTION

At present, for asymmetric flow patterns or when a plurality of flow patterns coexist, the measurement accuracy of the multiphase flow meter may be greatly reduced. A first object of the present invention is to improve the measurement accuracy of a multiphase flow meter under flow patterns of poor symmetry.

We know that the precision of nuclear medicine imaging based on gamma-rays has been relatively higher, with CT reaching a precision of 0.1 mm, SPECT and PET reaching 1.0 mm. If the density measurement of an object is undertaken in such high space precision, the analysis of the components of the mixture will be resolved easily. We may determine whether it is oil, gas or water according to a measurement density on each pixel rather than calculating an average density inside a narrow-beam cone like the present gamma-ray multiphase flow meter. We suppose that a mixture can be "quantized" to a single component in a very small volume. Such supposition is accurate on most pixels and may only bring a few errors on boundaries of a multiphase mixing. The biggest limitations of the application of nuclear medicine imaging in fluid are as follows: (1) the object of nuclear medicine imaging is static but the fluid is continuously changeable; (2) the final image of nuclear medicine is reconstructed by projection at many angles and the imaging speed is also often very low; (3) the nuclear medicine device consists of a plurality of detectors, and in order to obtain a multi-angle projection, the probe sometimes needs rotation for a large angle.

The present invention refers to a combination of a plurality of groups of detector arrays of nuclear medicine to increase numbers of effective detection zones of a conventional multiphase flow meter based on gamma-ray measurement technology (hereinafter briefly called as gamma multiphase flow meter) and reduce a space range of each detection zone. A reasonable detector array design may use many fairly small detection zones to cover cross-section of a whole oil pipeline so as to achieve full measurement rather than partial measurement. Just as the cross-section is bestrewed with many tiny gamma-ray flow meters from different angles, such high-precision full measurement no longer has requirements on the symmetry and homogeneity of fluid and thus also greatly improves its accuracy of measurement and adaptability to a multiphase flow of different flow patterns.

As the multiphase flow meter of the present invention uses a plurality of high-precision detector arrays, compared to the conventional gamma multiphase flow meter which uses a single probe, the method may acquire more information which comprises space distribution information of density of a multiphase flow. Due to limitations of cone measurement intervals of a conventional gamma multiphase flow meter, even for axially symmetric fluid, the cone measurement intervals of different sectorial angles may also provide different results. In other words, the measurement result is not absolutely independent on the measurement means or method and thus causes a relatively big measurement error. The multiphase flow meter which uses a plurality of high-precision detector arrays may reduce the measured intervals to many tiny independent pixel points, and thus avoids the asymmetric limitation of a conical measurement zone and greatly improves the confidence of a measurement value, which also pertain to a second object of the present invention.

A plurality of high-precision detector arrays may form a plurality of detection intervals each of which is determined by a pair of detectors and may acquire an average absorption coefficient of gamma-rays, and many average coefficients of different intervals acquired simultaneously may be used to reconstruct a density distribution condition of a multiphase flow on cross-sections of an oil pipeline, i.e. an instantaneous tomography image of fluid. Instantaneous tomography images obtained by temporally continuous measurement constitute dynamic videos of fluid. A cross-correlation processing may also be performed for tomography images obtained by two or more groups of detector arrays with certain spacing axially so as to acquire velocity information of fluid. The video information of fluid may provide basic metering data required in more effective reservoir management and production optimization, which also pertains to a third object of the present invention.

According to one aspect of the present invention, a positron tomography imaging apparatus for a multiphase flow in an oil pipeline is provided, characterized in that, the positron tomography imaging apparatus consists of at least one set of probes that can produce positron and electron annihilation and time-coincidence, each set of probes comprising a pair of parallel gamma-ray detector arrays, a positron radioactive source and a radioactive source shield, the pair of parallel gamma-ray detector arrays being respectively disposed on both sides of an oil pipeline under detection and being perpendicular to an axial direction of the oil pipeline, the positron radioactive source being located between the oil pipeline and a row of gamma-ray detector arrays in the pair of parallel gamma-ray detector arrays and parallel to the pair of parallel gamma-ray detector arrays, the radioactive source shield undertaking a gap shielding of the positron radioactive in the axial direction of the oil pipeline, the pair of parallel gamma-ray detector arrays included in the each set of probes determining a plurality of detection intervals, each of which is determined by a pair of gamma-ray detectors, an gamma-ray average absorption coefficient being acquired from each detection interval such that average absorption coefficients of different detection intervals acquired simultaneously are used to obtain an instantaneous tomography image of fluid.

The at least one set of probes consists of two sets of probes which constitute an orthogonal space structure to improve distributive homogeneity of the detection angles on cross-sections of the oil pipeline, the two sets of probes being mutually staggered in an axial direction to allow effective detection zones of the two sets of probes to be averted from each other so as to reduce a random coincidence and improve a signal-to-noise ratio of measurement.

The at least one set of probes consists of a plurality of sets of probes to improve a coverage range of effective detection zones on cross-sections of the oil pipeline, each adjacent two sets of probes having a rotation angle of 360°/N, and the plurality of sets of probes being mutually staggered in an axial direction to allow effective detection zones of the plurality of sets of probes to be averted from each other.

The positron radioactive source is a plurality of spotted positron radioactive sources, linear positron radioactive sources, or a combination source constituted by spotted positron radioactive sources and linear positron radioactive sources.

The gamma-ray detector is a semi-conductor ray detector, or scintillation crystal with a conventional photomultiplier, a position sensitive photomultiplier or a semiconductor photomultiplier.

The pair of parallel gamma-ray detector arrays of each set of probes simultaneously undertake time-coincidence of a prompt window and time-coincidence of a delay window, and the result of delay coincidence serves as a background noise which is deducted from a prompt coincidence result to improve a signal-to-noise ratio.

Two sets of the positron tomography imaging apparatuses are provided at certain spacing along an axial direction of the oil pipeline so as to acquire velocity information of the fluid by undertaking a continuous cross-correlation processing of a tomography images.

Instantaneous tomography images of fluid are temporally arranged in real time so as to obtain a tomography video of fluid.

The positron tomography imaging apparatus further comprises an image processing portion for processing the tomography image, which portion undertakes a single-phase quantization processing for pixels of the tomography image when an average absorption coefficient is close to a certain phase in a multiphase flow, recalculates an optimum value of an absorption coefficient of each remaining pixel after part of the pixels in the tomography image is quantized, and acquire phase fractions of a multiphase flow through multiple times of processing by quantization and optimum value evaluation so as to enable acquiring phase fractions, i.e. gas content, oil content and water content of a multiphase flow under a condition of single energy positron radioactive source.

According to another aspect of the present invention, a positron tomography imaging method for a multiphase flow in an oil pipeline is provided, characterized in that, undertaking a positron tomography imaging for the multiphase flow by using at least one set of probes that can produce positron and electron annihilation and time-coincidence, each set of probes comprising a pair of parallel gamma-ray detector arrays, a positron radioactive source and a radioactive source shield, the pair of parallel gamma-ray detector arrays being respectively disposed on both sides of an oil pipeline under detection and being perpendicular to an axial direction of the oil pipeline, the positron radioactive source being located between the oil pipeline and a row of gamma-ray detector arrays in the pair of parallel gamma-ray detector arrays and parallel to the pair of parallel gamma-ray detector arrays, the radioactive source shield undertaking a gap shielding of the positron radioactive in the axial direction of the oil pipeline, the pair of parallel gamma-ray detector arrays included in the each set of probes determining a plurality of detection intervals, each of which is determined by a pair of gamma-ray detectors, an average absorption coefficient being acquired from each detection interval such that average absorption coefficients of different detection intervals acquired simultaneously are used to obtain an instantaneous tomography image of fluid.

DETAILED DESCRIPTION OF EMBODIMENTS (1) Principles of Positron Tomography Imaging When gamma-ray with energy below 1 MeV interact with substance, there are mainly such two interactions as photoelectric effect and Compton effect. When photoelectric effect occurs, gamma photon gives all the energy to bound electron of the substance interacting therewith to allow it to be sent out by overcoming ionizing energy in atomic shell. The ompton effect should be a scattering between the gamma photon and the electron, in which the incidence gamma photon transfers part of the energy to the electron and the photon itself has a reduced energy and scatters towards different directions. Just as gamma photon interacts with substance, gamma-ray is absorbed and attenuated when passing the substance. When Compton effect occurs to the incidence gamma photon, the remaining energy and uncertain scattering direction of the photon allow it to be still possibly received by a detector such as to affect measurement of an absorption coefficient of gamma-rays. Thereby, narrow-beam gamma-ray is often used in application to reject scattering instances as much as possible so as to increase measurement accuracy. In order to realize a narrow-beam condition, it is necessary to undertake collimation screening of rays from a gamma source by a collimator. However, when high-precision detector array is used, each small detector needs a collimator and thus raises the design difficulty of a collimator, and at the same time many collimators may also have greatly reduced counting rate and sensitivity. If a system has a plurality of gamma sources which are distributed at positions of different angles and need collimation, the design difficulty thereof may be greater. If positron and electron annihilation technology is utilized, a collimator may be avoided and the counting rate is greatly improved.

Positron and electron annihilation may generate a pair of 180 degree opposing gamma photons simultaneously, each of which has a single energy of 511 keV so that we can use two opposing detectors to detect positron and electron annihilation instances. If each detected gamma-ray is discriminated by its full-energy peak in combination with time coincidence processing of gamma photon pairs, it is possible to relatively effectively reject scattering instances so as to improve measurement accuracy.

Figure 1:
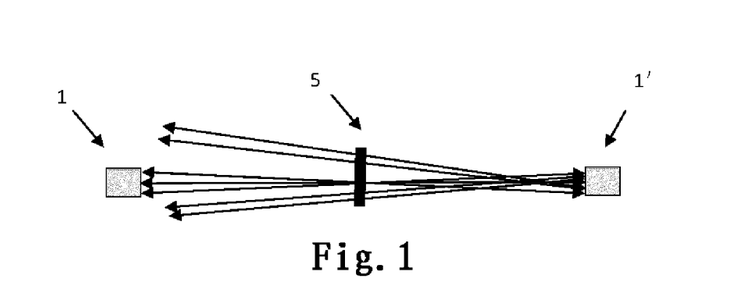
FIG. 1 indicates a collimation function of a positron and electron annihilation detector.

As shown in FIG. 1, detectors 1, 1' detect many gamma-rays generated by positron and electron annihilation from different angles, the gamma-rays are simultaneously detected by the detectors 1 and 1' within a quite small angle. Thus, if time coincidence processing is done to the detectors 1 and 1', namely, a collimation processing without a collimator is done to the detector 1' by using the detector 1, those annihilation instances detected by the detector 1 rather than by the detector 1' will be finally discriminated.

Figure 2:
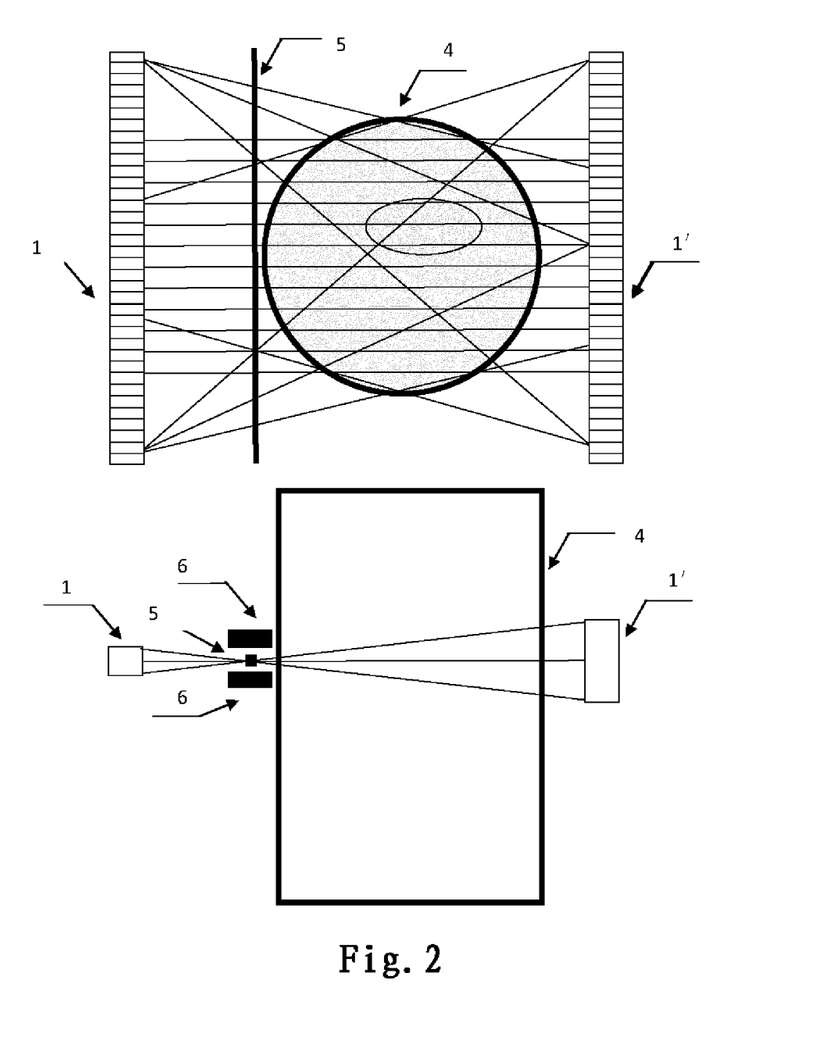
FIG. 2 is a schematic view of a multiphase flow positron tomography imaging apparatus, the upper half of which is a sectional view and the lower half of which is a top view.
Figure 3:
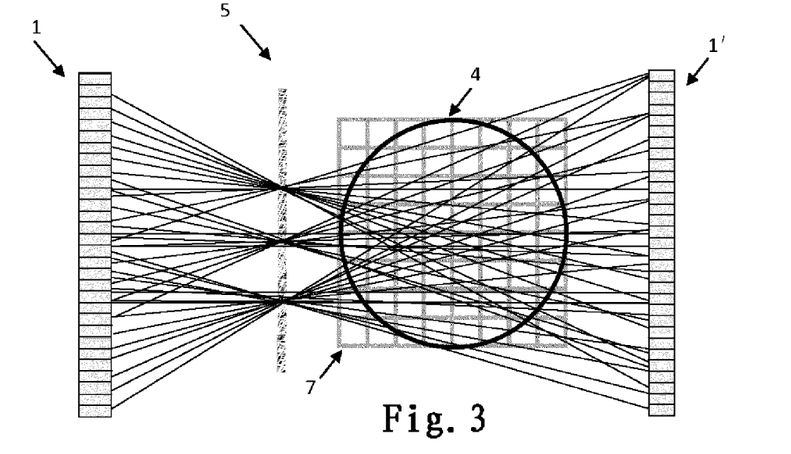
FIG. 3 is a schematic view of the principles of a multiphase flow positron tomography imaging.

FIG. 2 is a schematic view of the principles of a multiphase flow positron tomography imaging apparatus for a detected oil pipeline 4, the positron tomography imaging apparatus consisting of a set of probes that can generate positron and electron annihilations as well as time coincidence, the set of probes including a pair of parallel gamma-ray detector arrays 1, 1', a linear positron radioactive source 5 and a radioactive source shield 6. FIG. 2 has an upper half which is a sectional view and a lower half which is a top view, wherein a pair of parallel detector arrays 1, 1' are respectively located on both sides of the detected oil pipeline 4 and are perpendicular to an axial direction of the oil pipeline 4. The positron radioactive source 5 is located between the oil pipeline 4 and a row of detector arrays 1 thereof and parallel to the detector arrays 1, 1'. The radioactive source shield 6 undertakes gap shielding of the positron radioactive source 5 in an axial direction of the oil pipeline 4. The detectors in the gamma-ray detector arrays 1 and 1' are a semi-conductor ray detector, or scintillation crystal with a conventional photomultiplier, a position sensitive photomultiplier or a semiconductor photomultiplier. A pair of parallel gamma-ray detector arrays 1, 1' of each set of probes simultaneously undertake time coincidence of a prompt window and time coincidence of a delay window, and the result of delay coincidence serves as a background noise which is deducted from a prompt coincidence result to improve a signal-to-noise ratio of measurement. The linear positron radioactive source 5 may be regarded to be constituted by spotted positron radioactive sources at many different positions, and as shown in FIG. 3, if the tomography image of the oil pipeline is constituted by an image pixel matrix 7, each pixel will probably be measured by a plurality of sets of detector pairs at the same time. Each detector pair represents a different detection angle, and thus each pixel will have measurements from many different angles. When two sets of N detector arrays use a conventional measurement method, there are only 2N detection tracks which provide 2N attenuation absorption equations, while the positron and electron annihilation method of the present invention may provide $N^2$ attenuation absorption equations. The more constraint equations there are, the higher the measurement accuracy of the multiphase flow meter will be, the more the pixels of an allowable sectional image will be, and the higher the precision of the image will be.

Figure 4:
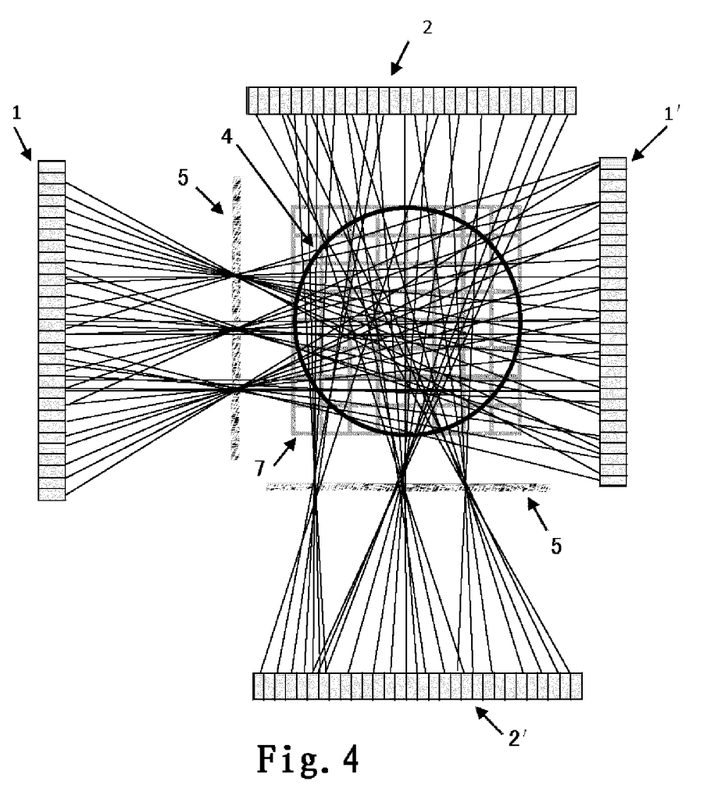
FIG. 4 is a schematic view of an orthogonal probe structure of a multiphase flow positron (linear positron radioactive source) tomography imaging.
Figure 5:
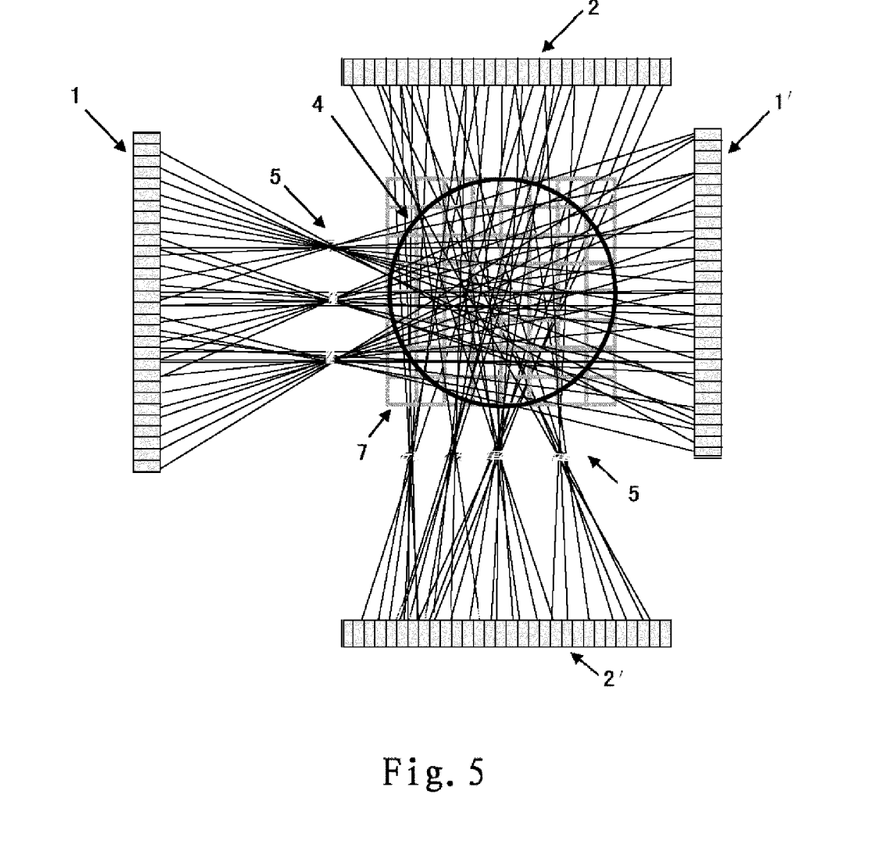
FIG. 5 is a schematic view of an orthogonal probe structure of a multiphase flow positron (a plurality of spotted positron radioactive sources) tomography imaging.
Figure 6:
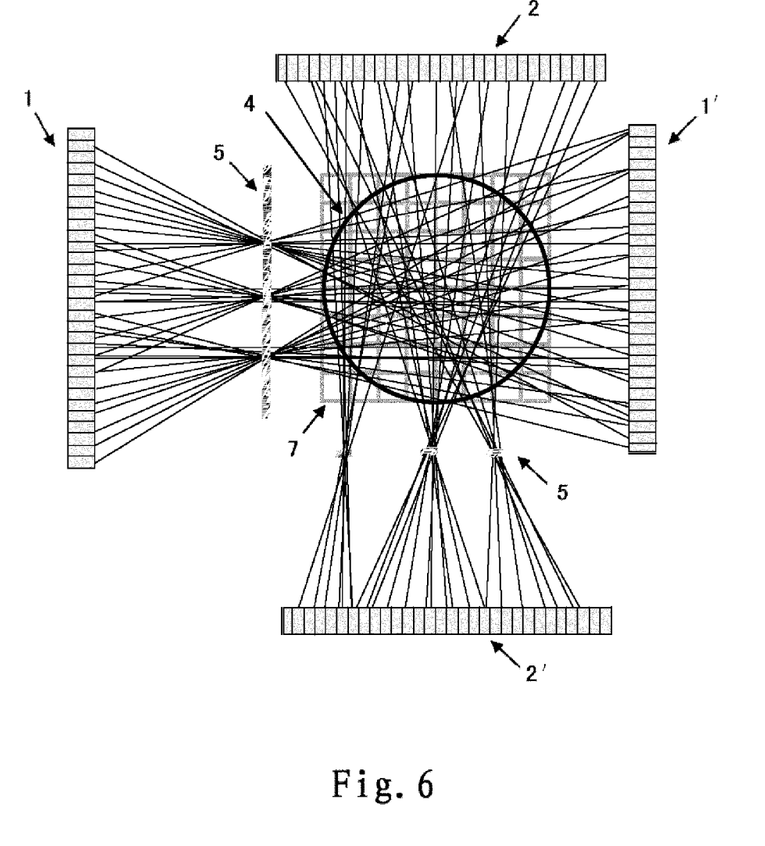
FIG. 6 is a schematic view of an orthogonal probe structure of a multiphase flow positron (a positron radioactive source mixing a spotted pattern and a linear pattern) tomography imaging.
Figure 7:
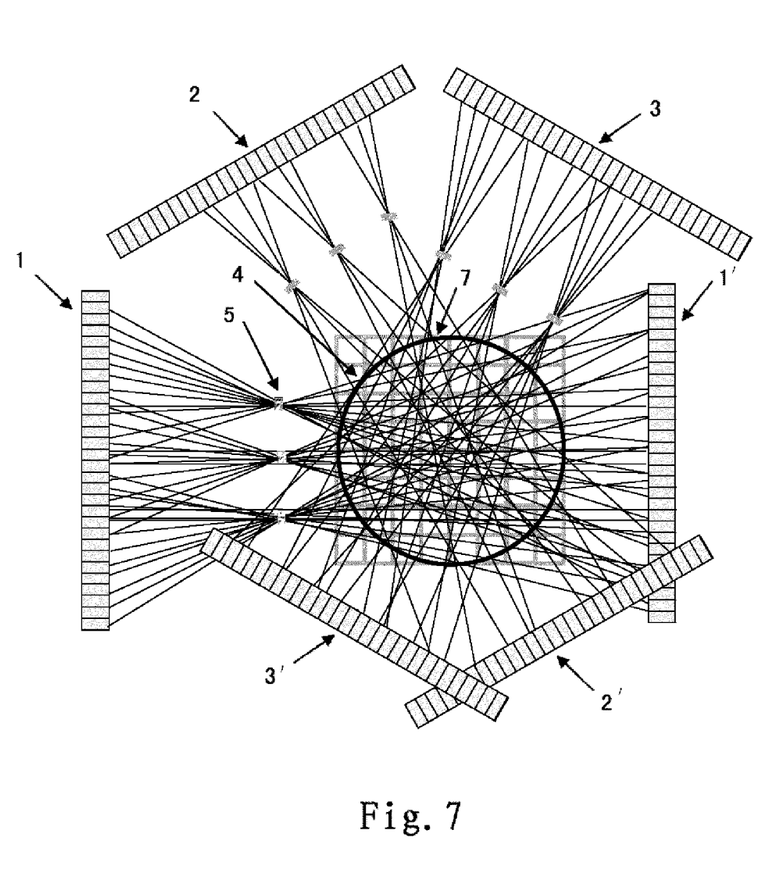
FIG. 7 is a schematic view of an axially three-set probe structure of the multiphase positron imaging apparatus.

In order to improve homogeneous distribution of a plurality of measurement angles of each pixel within 360 degrees on a cross-section, the multiphase flow meter of the present invention may be constituted by two or more sets of positron and electron annihilation coincidence probes, each set of which comprises a pair of parallel detector arrays, positron radioactive source and radioactive source shield. If there are two sets of positron and electron annihilation coincidence probes, it is possible to compose an orthogonal structure, in which one set of probes will reach an angle of the other set by rotating about an axle centre of the oil pipeline for 90 degrees, but such two sets of probes are staggered to certain extent at axial positions of the oil pipeline so as to avoid effective detection intervals of the opposing probe. FIGS. 4, 5 and 6 respectively provide schematic views of orthogonal structures of a mixed source constituted by linear positron radioactive source 5, a plurality of spotted positron radioactive sources 5, or a combination source of linear positron radioactive sources and spotted positron radioactive sources. For N sets of probes, each adjacent two sets of detector arrays has a rotation angle of 360/N, and axially avoids detection intervals of other detector arrays. FIG. 7 provides a structural view of axially having three sets of positron detector arrays 1, 1', 2, 2', 3 and 3'.

Positron radioactive source may use Ge-68 (the half-life of which is 271 days), Na-22 (the half-life of which is 2.6 years) or other sources. When the intensity of the radioactive source is strengthened, it is possible to detect false random coincidence instances from a plurality of different positron and electron annihilations within certain coincidence time window. Such false random coincidence instances increase background of measurement and thus may finally affect precision of density detection. In order to eliminate the background, we use another time window having a fixed time delay but the same duration to measure a counting of random coincidence, which counting is used as a background that is deducted from the aforementioned prompt coincidence instances. It is necessary to carry out a gap shielding of positron sources in an axial direction to reduce single instance rate so as to reduce processing dead time of detector electronics, improve coincidence efficiency of actual instances and reduce random coincidence rate.

(2) Tomography Imaging

With reference to a combination of a plurality of detector arrays of nuclear medicine, it is possible to increase the number of effective detection intervals of a conventional gamma-ray multiphase flow meter and reduce the detection space range of each detection space. As shown in FIG. 3, suppose there are M pixels within a cross-section of the oil pipeline, the connection of each pair of detectors may pass through a plurality of pixels so that an average absorption coefficient measured by such pair of detectors represents an average absorption coefficient of all the pixels on the track (there is only one equation but a plurality of unknown variables) rather than an absorption coefficient of a single pixel. However, if we have in total L detector pairs passing though cross-sections of the oil pipeline, then we have L equations to evaluate M unknown variables, and if L>M, it is possible to acquire an optimum solution of M unknown variables and thus to represent a fluid section image by using an average absorption coefficient of pixels. The image of the absorption coefficient is similar to a tomography image of CT.

A plurality of high-precision detector arrays may form a plurality of detection intervals, each interval is determined by a pair of detectors, each interval will acquire an average absorption coefficient of gamma-ray, and many average absorption coefficients of different intervals acquired simultaneously may be used to reconstruct density distribution condition of fluid on a cross-section of the oil pipeline, i.e. an instantaneous tomography image of fluid. The instantaneous tomography image obtained by a temporally continuous measurement constitutes a dynamic image of fluid, which can provide a more effective reservoir management and production optimization management for production. A cross-correlation processing may also be performed for the tomography images obtained by two or more sets of detector arrays disposed at certain spacing along an axial direction of the oil pipeline so as to obtain flow velocity information of the fluid.

(3) Acquisition of Phase Fraction

The aforementioned tomography image generated by positron and electron annihilation consists of absorption coefficients of a plurality of pixels. The absorption coefficient matrix of such pixels is an optimum solution for satisfying measurement values of all the detectors, and the average absorption coefficient of each pixel acquired thereby is often a continuous value. As the absorption coefficient is a function of the fluid density, for example water and oil as shown in the following table have different absorption coefficients for gamma-rays of the same energy.

Absorption coefficients (m) of water and oil for narrow beam gamma-rays of different energy (experimental value)

| Energy (keV) | Water | Oil |
|---|---|---|
| 75-80 | 0.159 | 0.142 |
| 167 | 0.137 | 0.118 |
| 364 | 0.099 | 0.092 |

If it is made by two-phase mixing at certain percentage in certain pixel space, its average absorption coefficient is a value between two absorption coefficients of the two-phase. For a two-phase fluid, it only needs a known average absorption coefficient such as to obtain a respective phase fraction of the two-phase in the pixel. However, for a three-phase (oil, gas or water) mixture and even a four-phase (oil, gas, water and sand) mixture, there is only one average coefficient in each pixel, which is inadequate to evaluate a phase fraction of its respective phase.

However, if the precision of an image is high enough, or the size of the pixel is small enough, the fluid within such tiny pixel intervals will probably be "quantized" to become a single phase. If it is a pixel of a single fluid phase, the solved absorption coefficient will be close to an actual absorption coefficient of certain phase in oil, gas or water, the image processing portion of the positron tomography imaging apparatus is used to "quantize (determine)" the pixel to the single phase so that the continuous value of the initially calculated absorption coefficient in the pixel will be "quantized". When the pixel of the image portion is "quantized (determined)", it is necessary to recalculate an optimum value of an absorption coefficient of each remaining pixel. After a plurality of cycles of calculation-quantization-recalculation, only several pixels positioned two-phase boundaries are probably indefinite and thus a multiphase problem will become a two-phase solvable problem. The pixels of such boundaries according to the components of the adjacent pixels will probably become such two-phase solvable problems as oil and water, oil and gas, and water and gas. Therefore, a multiphase meter having an imaging function may only depend on a single-energy radioactive source rather than a dual-energy radioactive source such as to calculate a phase fraction (gas content, oil content and water content) of a multiphase flow. As the extraction of the aforementioned phase fraction determines components of each pixel according to relative densities between image pixels rather than according to an absolute counting which requires comparing with calibrated counting, the effects of such parameters as decay of positron source and ambient temperature over the measurement result may be greatly reduced. Thereby, a single-energy multiphase flow meter based on an image may greatly reduce the complication degree of the designing of the system and improve the reliability.

(4) Tomography Video and Flow Velocity of Fluid

If the continuous multi-frame tomography images output by the positron tomography imaging apparatus are temporally arranged in real time, they will become tomography videos of the fluid. Further, the detected oil pipeline is respectively mounted with two sets of the apparatuses that are capable of synchronously outputting tomography images, and a cross-correlation processing is undertaken for the two sets of tomography images to obtain flow velocity information of fluid. Suppose the interframe gap is M, and the continuous cross-correlation output of the two sets of images reaches maximum, the flow velocity of fluid V=the gap of the two sets of imaging apparatuses L/((sampling time of single-frame)×M).

The invention claimed is:

1. A positron tomography imaging apparatus for a multiphase flow in an oil pipeline, comprising at least one set of probes configured to produce positron and electron annihilation and detect time-coincidence gamma ray events, wherein each set of probes comprises a pair of parallel gamma-ray detector arrays, a positron radioactive source and a radioactive source shield, wherein the pair of parallel gamma-ray detector arrays are configured to be respectively disposed on both sides of an oil pipeline under detection and perpendicular to an axial direction of the oil pipeline, the positron radioactive source configured to be located between the oil pipeline and a row of gamma-ray detector arrays in the pair of parallel gamma-ray detector arrays and parallel to the pair of parallel gamma-ray detector arrays, the radioactive source shield configured to undertake a gap shielding of the positron radioactive source in the axial direction of the oil pipeline, the pair of parallel gamma-ray detector arrays in each set of probes configured to determine a plurality of detection intervals, each of which is determined by a pair of gamma-ray detectors, wherein an average absorption coefficient of gamma-ray is acquired from each detection interval such that average absorption coefficients of different detection intervals acquired simultaneously may be used to reconstruct a tomography image of fluid.

2. The positron tomography imaging apparatus according to claim 1, wherein the at least one set of probes comprises two sets of probes which constitute an orthogonal space structure to improve distributive homogeneity of detection angles on cross-sections of the oil pipeline, the two sets of probes being mutually staggered in an axial direction to allow effective detection zones of the two sets of probes to be averted from each other so as to reduce a random coincidence and improve a signal-to-noise ratio of measurement.

3. The positron tomography imaging apparatus according to claim 1, wherein the at least one set of probes comprises a plurality of sets of probes to improve a coverage range of effective detection zones on cross-sections of the oil pipeline, each adjacent two sets of probes having a rotation angle of 360°/N, and the plurality of sets of probes being mutually staggered in an axial direction to allow effective detection zones of the plurality of sets of probes to be averted from each other.

4. The positron tomography imaging apparatus according to claim 1, wherein the positron radioactive source is a plurality of spotted positron radioactive sources, linear positron radioactive sources, or a combination source constituted by spotted positron radioactive sources and linear positron radioactive sources.

5. The positron tomography imaging apparatus according to claim 1, wherein the gamma-ray detector is a semi-conductor ray detector, or scintillation crystal with a conventional photomultiplier, a position sensitive photomultiplier or a semiconductor photomultiplier.

6. The positron tomography imaging apparatus according to claim 1, wherein the pair of parallel gamma-ray detector arrays of each set of probes are configured to simultaneously undertake time-coincidence detection of gamma events by a prompt window and time-coincidence of a delay window, a coincidence result of the delay window as a background noise being deducted from a coincidence result of the prompt window to improve a signal-to-noise ratio of measurement.

7. A method of acquiring flow velocity information of fluid in a pipeline comprising:
providing two positron tomography imaging apparatuses according to claim 1 at certain spacing along an axial direction of the oil pipeline, and
acquiring flow velocity information of the fluid by undertaking a continuous cross-correlation processing of tomography images.

8. A method of obtaining a tomography video of fluid comprising temporally arranging instantaneous tomography images of fluid acquired with a positron tomography imaging apparatus according to claim 1 in real time so as to obtain a tomography video of fluid.

9. The positron tomography imaging apparatus according to claim 1, wherein the positron tomography imaging apparatus further comprises an imaging processing portion configured to process the tomography image, which comprises a single-phase quantization processing of pixels of the tomography image when an average absorption coefficient is close to a certain phase in a multiphase flow, recalculation of an optimum value of an absorption coefficient of each remaining pixel after part of the pixels in the tomography image is quantized, and acquisition of a phase fraction of a multiphase flow through multiple times of processing by quantization and optimum value evaluation so as to enable acquisition of a phase fraction of a multiphase flow under a condition of monoenergetic positron radioactive source.

10. The positron tomography imaging apparatus according to claim 9, wherein the phase fraction is selected from the group consisting of gas content, oil content and water content.

11. A positron tomography imaging method for a multiphase flow in an oil pipeline comprising: positron tomography imaging providing the positron tomography imaging apparatus of claim 1; determining the plurality of detection intervals; simultaneously acquiring the average absorption coefficients of different detection intervals; and reconstructing the tomography image from the average absorption coefficients.

* * * * *